(12) United States Patent
Choi et al.

(10) Patent No.: US 9,019,097 B2
(45) Date of Patent: Apr. 28, 2015

(54) MEDICATION SERVICE APPARATUS, MEDICATION BOX, AND APPARATUS AND METHOD FOR ASSISTING MEDICATION

(75) Inventors: Jae Hun Choi, Daejeon (KR); Myung Eun Lim, Daejeon (KR); Sun Lee Bang, Daejeon (KR); Dae Hee Kim, Daejeon (KR); Soo Jun Park, Seoul (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1041 days.

(21) Appl. No.: 12/482,792

(22) Filed: Jun. 11, 2009

(65) Prior Publication Data
US 2010/0123576 A1 May 20, 2010

(30) Foreign Application Priority Data
Nov. 18, 2008 (KR) ........................ 10-2008-0114899

(51) Int. Cl.
| | |
|---|---|
| G08B 1/08 | (2006.01) |
| G08B 23/00 | (2006.01) |
| G08B 1/00 | (2006.01) |
| G07F 9/02 | (2006.01) |
| A61J 7/00 | (2006.01) |
| A61J 7/04 | (2006.01) |
| G06F 19/00 | (2011.01) |
| G07F 11/16 | (2006.01) |
| G07F 11/62 | (2006.01) |
| G07F 17/00 | (2006.01) |

(52) U.S. Cl.
CPC .............. *G07F 9/026* (2013.01); *A61J 7/0084* (2013.01); *A61J 7/0481* (2013.01); *A61J 2007/0418* (2013.01); *A61J 2007/0427* (2013.01); *A61J 2007/0445* (2013.01); *A61J 2007/0454* (2013.01); *A61J 2007/0463* (2013.01); *A61J 2007/049* (2013.01); *G06F 19/3462* (2013.01); *G07F 11/16* (2013.01); *G07F 11/62* (2013.01); *G07F 17/0092* (2013.01)

(58) Field of Classification Search
None
See application file for complete search history.

(56) References Cited

U.S. PATENT DOCUMENTS

| | | | |
|---|---|---|---|
| 5,289,157 A | 2/1994 | Rudick et al. | |
| 6,107,911 A | 8/2000 | Perrone | |
| 6,163,736 A * | 12/2000 | Halfacre | ........................ 700/232 |

(Continued)

FOREIGN PATENT DOCUMENTS

| | | |
|---|---|---|
| EP | 1 857 088 A1 | 11/2007 |
| EP | 1 857 089 A1 | 11/2007 |

(Continued)

*Primary Examiner* — Julie Lieu
(74) *Attorney, Agent, or Firm* — Ladas & Parry LLP

(57) ABSTRACT

An apparatus and method for assisting medication are disclosed. The apparatus includes a medication box and a medication service device. The medication box includes a plurality of containers each storing a paper bag of medication, and discharges a paper bag of medication from a corresponding one of the containers using a rotational force of an electric motor, and detects whether the stored paper bag of medication is present or is discharged. The medication service device includes a situation detector detecting a status of a user based on user identification and signal strength included in a radio frequency signal, and a status of the medication box, a situation recognizer recognizing a medication situation, and a service executor generating a service for medication. The user who has to regularly take a paper bag of medication for a long time can be assisted to take an accurate dose of medication on time.

19 Claims, 9 Drawing Sheets

(56) References Cited

U.S. PATENT DOCUMENTS

| | | | |
|---|---|---|---|
| 7,002,476 B2 * | 2/2006 | Rapchak | 340/573.1 |
| 7,755,478 B2 * | 7/2010 | Niemiec et al. | 340/539.12 |
| 8,044,778 B2 * | 10/2011 | Monroe | 340/426.19 |
| 8,108,068 B1 * | 1/2012 | Boucher et al. | 700/236 |
| 2002/0109601 A1 * | 8/2002 | Arens | 340/573.1 |
| 2002/0149472 A1 * | 10/2002 | Roe | 340/309.15 |
| 2004/0104271 A1 | 6/2004 | Martucci et al. | |
| 2004/0243445 A1 * | 12/2004 | Keene | 705/2 |
| 2005/0131397 A1 * | 6/2005 | Levin | 606/1 |
| 2006/0058917 A1 * | 3/2006 | Vonk et al. | 700/236 |
| 2008/0231452 A1 * | 9/2008 | Levin | 340/572.1 |
| 2011/0202174 A1 | 8/2011 | Bogash et al. | |

FOREIGN PATENT DOCUMENTS

| | | |
|---|---|---|
| JP | 2005-013488 A | 1/2005 |
| KR | 20040073560 A | 8/2004 |
| KR | 1020070001285 A | 1/2007 |
| KR | 2020080001892 A | 6/2008 |

\* cited by examiner

MEDICATION SERVICE APPARATUS, MEDICATION BOX, AND APPARATUS AND METHOD FOR ASSISTING MEDICATION

CROSS-REFERENCE TO RELATED APPLICATIONS

This application claims, under 35 U.S.C. §119(a), the benefit of Korean Patent Application No. 2008-114899 filed on Nov. 18, 2008, in the Korean Intellectual Property Office, the disclosure of which is incorporated herein by reference in its entirety.

BACKGROUND OF THE INVENTION

1. Field of the Invention

The present invention relates to medication assist, and more particularly, to a medication service device, a medication box, and apparatus and method for assisting medication that assist and encourage individuals to regularly take medications in their daily lives.

2. Description of the Related Art

Patients with chronic illness and the elderly have to continually take medications on a regular schedule in the daily lives.

However, the elderly may have difficulty in following medication (i.e., continuously taking medication on schedule) due to memory failure. For this reason, many regimens have recently been developed for systematically assisting medication such that the elderly can readily adapt themselves to medication schedules and take an accurate dose of medication on time.

The regimens for assisting medication that have been developed have turned out to be considerably effective when actually applied to the elderly.

Among the regimens for enhancing medication, a representative regimen includes an apparatus for assisting medication, such as a medication bottle or box to which a clock and an alarm are attached. If a time to take a medication is set, this apparatus for assisting medication informs the user to take the medication via sound or voice at the set time. Other regimens provide apparatuses, each of which uses a sensor and a communication device attached to a medication box to transmit a medication situation to a server. Each of these apparatuses with the sensor mounted on a cover regards an individual as having taken his or her medication when the cover is open, and manages the medication situation of the individual by transmitting the medication situation to the server.

Individual doses of medications to be taken at one time, formulated according to prescriptions, are generally provided to patients in the form of a small sealed bag in order to prevent patients from taking an incorrect medication. However, the conventional apparatuses cannot afford a service for individually packaged doses of medications. In addition, the conventional apparatuses do not count on a case where one user is required to take several types of medications per day. For example, a user may take different medications for one disease in the morning, noon and evening, as well as other different types of medications every day for a different medical condition or disease such as hypertension, diabetes, heart disease, etc. However, the conventional apparatuses are not designed in consideration of these cases.

Furthermore, the conventional apparatuses are designed to store and service some medications that can be taken over a short period. In the case of long-term medication for a chronic disease, the conventional apparatuses have a problem in distributing medications every day.

Moreover, the conventional apparatuses carry out a medication service regardless of the situations of the individuals utilizing them. For example, when an individual is out with medications, the conventional apparatuses cannot afford to perform a suitable service.

SUMMARY OF THE INVENTION

An aspect of the present invention provides an apparatus and method for assisting medication, a medication service device and a medication box that assist and encourage individuals to take a medication packaged in a paper bag at regular intervals.

Another aspect of the present invention provides an apparatus and method for assisting medication, a medication service device and a medication box that assist and encourage a user to take several types of medications according to schedules.

A further aspect of the present invention provides an apparatus and method for assisting medication, a medication service device and a medication box that afford a service in cooperation with a server that can recognize the medication situation of a user using a user recognition device as well as managing overall medication data via the Internet.

According to an aspect of the present invention, the apparatus for assisting medication may include a medication box comprising a plurality of containers, each storing a paper bag of medication, wherein the medication box discharges a paper bag of medication from a corresponding one of the containers using a rotational force of an electric motor, and detects whether or not the stored paper bag of medication exists and whether or not the stored paper bag of medication is discharged; and a medication service device. The medication service device includes a situation detector detecting a status of a user based on user identification and signal strength included in a radio frequency signal, received from a user recognition device carried by the user, and a status of the medication box; a situation recognizer recognizing a medication situation based on status data detected by the situation detector; and a service executor generating a service for medication based on the recognized medication situation and affording the generated service.

According to another aspect of the present invention, the medication service device may include a situation detector detecting a status of a user based on user identification and signal strength included in a radio frequency signal, received from a user recognition device carried by the user, and a status of a medication box storing a paper bag of medication; a situation recognizer recognizing a medication situation based on status data detected by the situation detector; and a service executor generating a service for medication based on the recognized medication situation and affording the generated service.

According to another aspect of the present invention, the medication box may include a plurality of containers each having a cover and an input port formed in the cover, through which a paper bag of medication is inputted, wherein each of the containers stores the paper bag of medication, detects a presence of the stored paper bag of medication, and if the stored paper bag of medication is present, discharges the stored paper bag of medication according to a medication schedule; a discharge port discharging the paper bag of medication from the container; a button discharging the paper bag of medication stored in the container; and a display announcing the discharge of the paper bag of medication.

According to another aspect of the present invention, the method for assisting medication is carried out by a medication service device in a system for assisting medication, which includes the medication service device and a medication box storing paper bags of medication. The method may include detecting a status of a user and a status of the medication box; recognizing a medication situation based on detected status data; generating a service according to the recognized medication situation; and visualizing and providing the generated service.

According to another aspect of the present invention, the method for assisting medication is carried out by a medication box in a system for assisting medication, which includes the medication box storing paper bags of medication and a medication service device. The method may include, when a discharge command is received according to a medication schedule generated by the medication service device, detecting whether or not a paper bag of medication is present in a corresponding container using a sensor disposed in the container; if a paper bag of medication is detected in the container, driving an electric motor disposed inside the container and discharging the paper bag of medication using a rotational force of the electric motor; and detecting whether or not the paper bag is discharged and providing a notification service according to a result of the detection.

According to embodiments of the invention, a user who has to regularly take a paper bag of medication for a long time can be assisted and encouraged to take an accurate dose of medication according to schedule. Thereby, the adaptability of the user for medication can be remarkably improved, and the medical costs associated with curing a disease may be greatly reduced.

BRIEF DESCRIPTION OF THE DRAWINGS

The above and other aspects, features and advantages of certain exemplary embodiments of the present invention will be more apparent from the following description taken in conjunction with the accompanying drawings, in which.

DETAILED DESCRIPTION OF EXEMPLARY EMBODIMENTS

The present invention will now be described more fully hereinafter with reference to the accompanying drawings, in which exemplary embodiments thereof are shown. In the following description of the present invention, a detailed description of known functions and components incorporated herein will be omitted when it may make the subject matter of the present invention rather unclear.

In the detailed description of exemplary embodiments of the invention, a system and method for assisting medication that can assist individuals who are required to regularly take medication in their daily lives will be described. Firstly, a detailed description will be given of the construction of the system for assisting medication in accordance with an exemplary embodiment of the invention with reference to the accompanying drawings.

Figure 1:
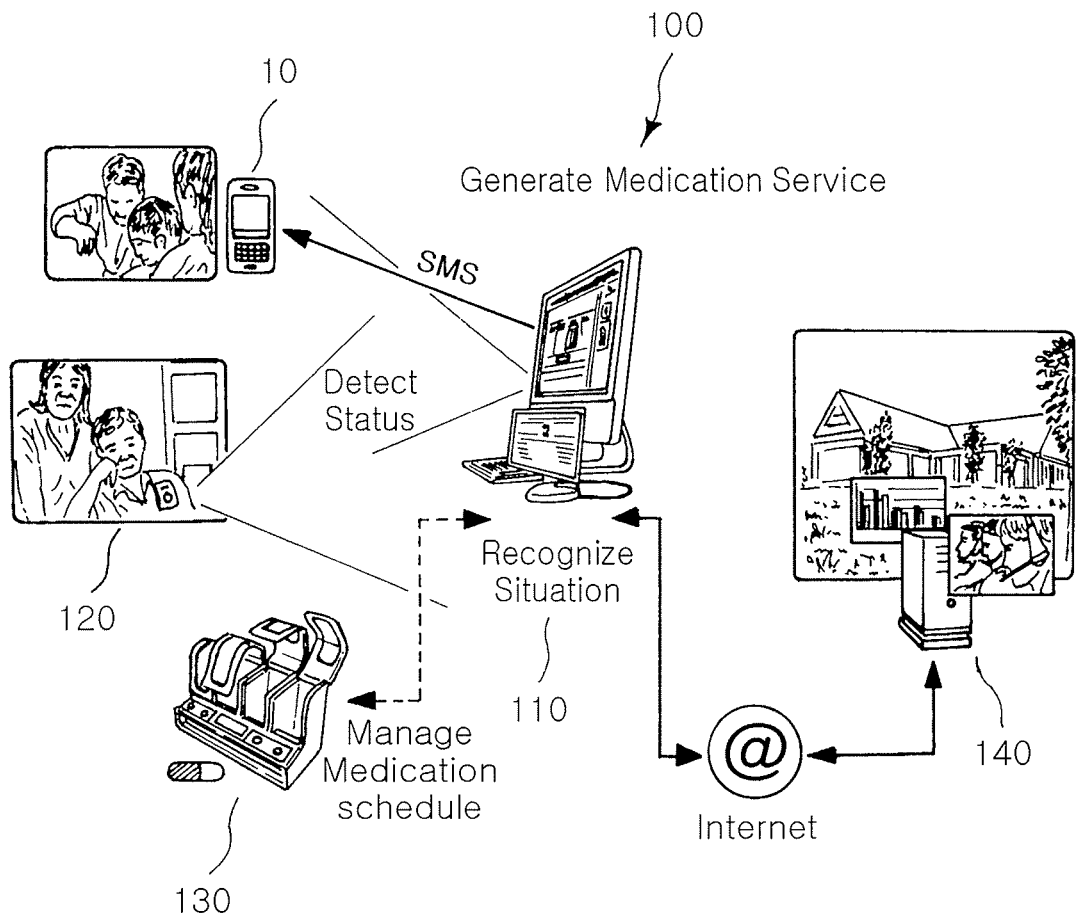
FIG. 1 is a conceptual configuration view illustrating a system for assisting medication in accordance with an exemplary embodiment of the invention.
Figure 2:
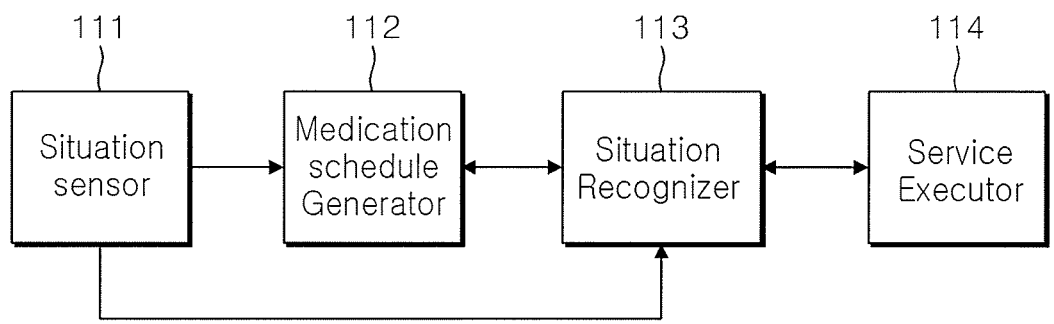
FIG. 2 is a block diagram illustrating a detailed configuration of a medication service device in accordance with an exemplary embodiment of the invention.

FIG. 1 is a conceptual configuration view illustrating a system for assisting medication in accordance with an exemplary embodiment of the invention.

Referring to FIG. 1, the system for assisting medication 100 includes a medication service device 110 communicating with a portable device 10, a user recognition device 120, a medication box 130 and a server 140. The medication service device 110 and the medication box 130 can be combined into one unit, which hereinafter will be referred to as an apparatus for assisting medication. In this embodiment of the invention, the medication service device 110 and the medication box 130 will be described separately for the sake of convenience.

The medication service device 110 includes a situation sensor 111, a medication schedule generator 112, a situation recognizer 113 and a service executor 114.

The situation sensor 111 detects the status of an individual based on a radio signal transmitted from the user recognition device 120, and detects the state of the medication box 130 based on a plurality of signals received from the medication box 130. Specifically, the situation sensor 111 acquires user Identification (ID) and signal strength (RF strength) from a received RF signal in order to detect the state of the user. Then, the situation sensor 111 identifies the user by acquiring the confirmed user ID from a preset user mapping table as shown in Table 1, and determines distance from the user by acquiring the confirmed signal strength from a preset distance mapping table as shown in Table 2.

TABLE 1

| User | ID |
|------|----|
| A | 1 |
| B | 2 |
| ... | ... |

TABLE 2

| RF (dBm) | Distance (m) | Situation |
|----------|--------------|-----------|
| 90~75 | 0~1 | Adjacent |
| 75~alpha | 1~7 | Confirmed |
| Alpha< | 7~8 | Not confirmed |

The situations in Table 2 are divided into "Adjacent," "Confirmed" and "Not confirmed" according to the distance. In Table 2, "Adjacent" indicates a status where the user is adjacent to the smart medication box 130 and thus can be provided with a delicate medication service. "Confirmed" indicates a status where the user is at a distance from which he/she can recognize a general medication service performed by a screen or a voice message. "Not confirmed" indicates a status where the user cannot be provided with a general medication service. In this case, it is required to afford a special service such as a short message or a telephone call via the portable device 10.

In addition, the situation sensor 111 searches for a medication schedule for the recognized user from previously-stored medication schedules, which were generated by the medication schedule generator 112, and detects information such as medication box ID, a container status (i.e., whether or not a medication is present in the box), a discharge command (i.e., whether or not a button is pushed), a motor (i.e., whether or not the motor is rotating) and a Liquid Crystal Display (LCD) in order to determine the status of the medication box. Therefore, the situation detector 111 transfers status data (i.e., the recognized user, the acquired distance and medication schedule, and information acquired by detecting the status of the medication box) to the situation recognizer 113.

The medication schedule generator 112 receives prescription data for the corresponding medication and automatically generates a medication schedule using the received prescription data.

The situation recognizer 113 receives the status data, obtained by detecting the status of the user and the medication box, from the situation recognizer 111, and recognizes a medication situation using the received status data.

The service executor 114 affords a medication service to the user. Specifically, the service executor 114 generates and visualizes a variety of services such as a notification of medication according to the medication situation recognized by the situation recognizer 113.

Figure 3:
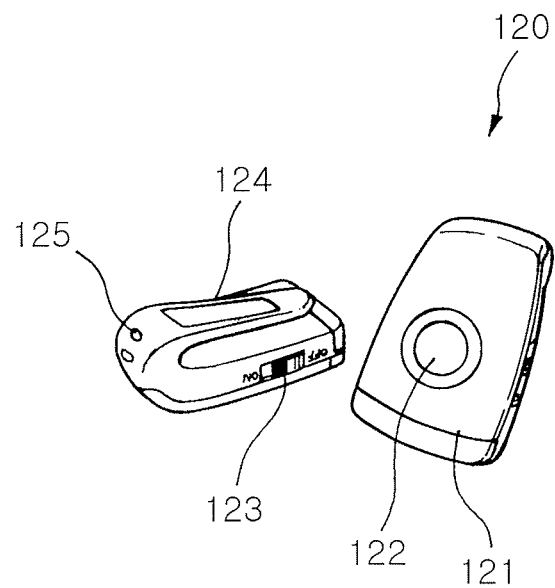
FIG. 3 is a perspective configuration view illustrating a user recognition device in accordance with an exemplary embodiment of the invention.

As shown in FIG. 3, the user recognition device 120 includes a body 121, a unit 122 for transmitting RF signals and confirming battery status, a power switch 123 and a holding part 124 and 125, a detailed description of which will be omitted.

Figure 4:
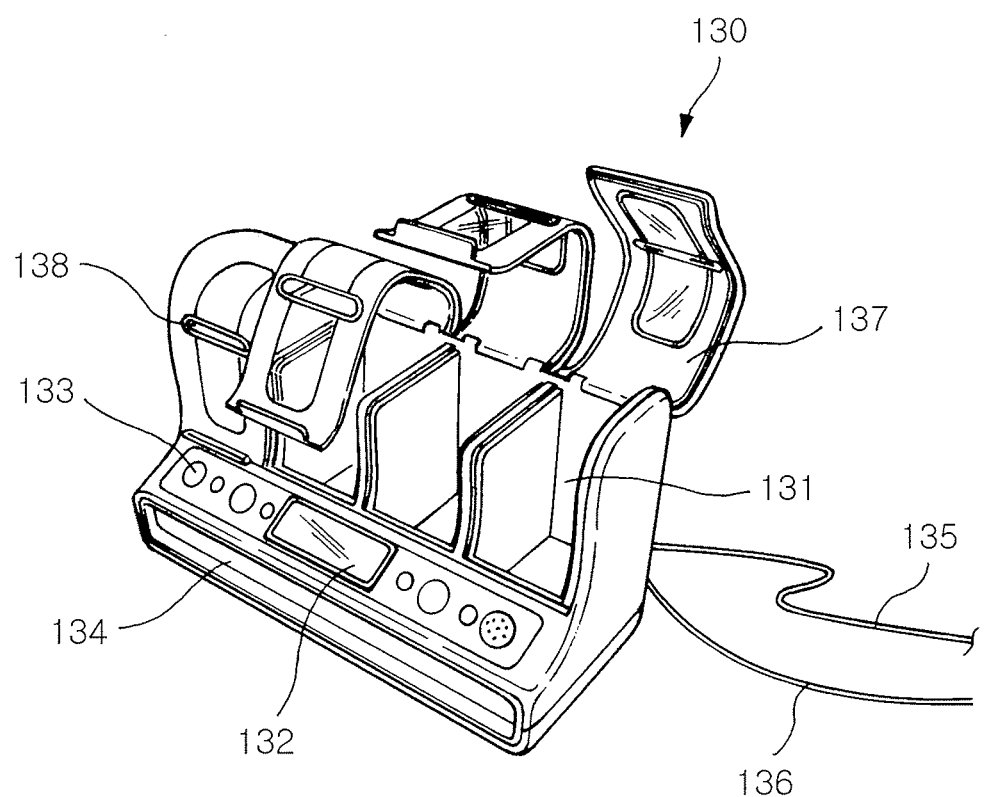
FIG. 4 is a perspective view illustrating a detailed configuration of a medication box in accordance with an exemplary embodiment of the invention.

The medication box 130 can be configured as shown in FIG. 4. The smart medication box 130 includes a plurality of containers 131, a displaying part 132 (e.g., an LCD), a discharge button 133, a discharge port 134, a power line 135 and a connection line 136 connecting the medication box 130 to an outer device (not shown). Each of the containers 131 has a cover 137, and one input port 138 is formed in the cover 137. As described above, the medication box 130 can be provided integrally with the medication service device 110. In this case, the medication box 130 is required to have an Internet or telephone line. In the case where the medication box 130 is provided as a separate part, it can be connected to an external computer via a Universal Serial Bus (USB) port.

Figure 5:
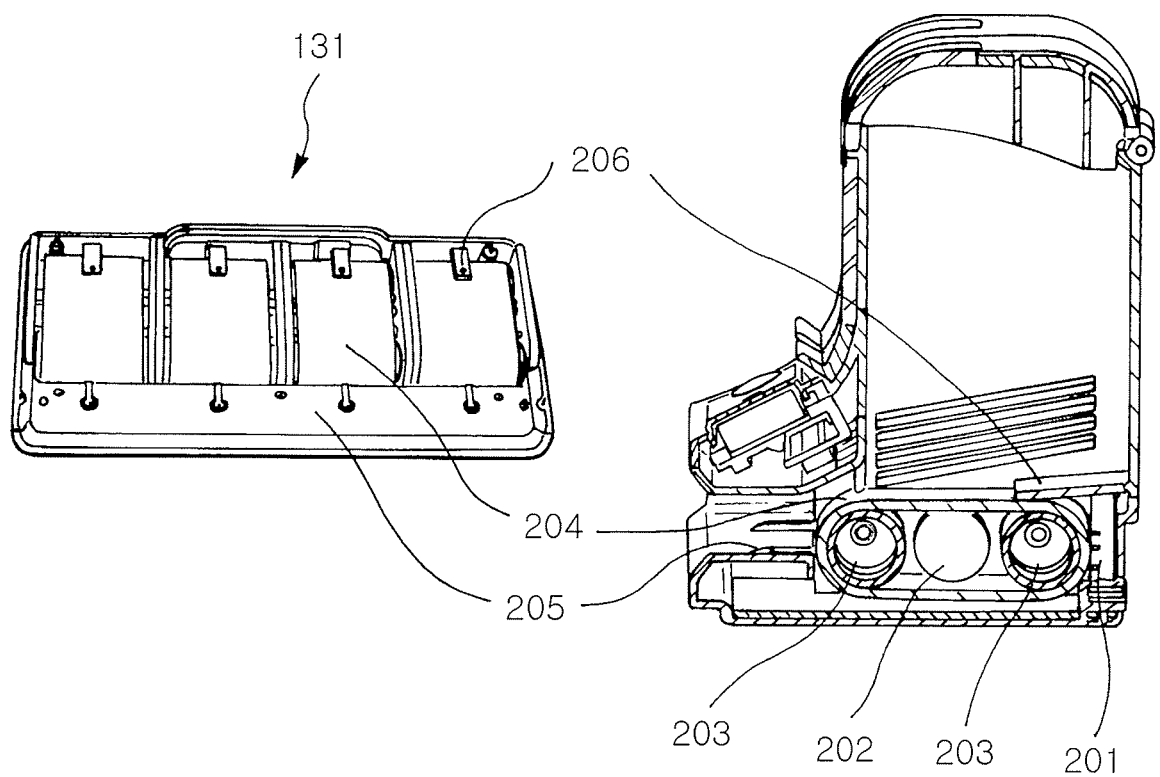
FIG. 5 is a view illustrating the internal structure of the medication box in accordance with an exemplary embodiment of the invention.

As shown in FIG. 5, each of the containers 131 includes a container controller 201, an electric motor 202, rotary shafts 203, a silicone belt 204 and first and second sensors 205 and 206.

The container controller 201 is configured as a Printed Circuit Board (PCB) with a processor and a memory attached thereto to control the overall operation of the medication box 130 and discharge a corresponding medication.

The electric motor 202 rotates the silicone belt 204 to move a paper bag of medication until the paper bag of medication touches the second sensor 206, and the rotary shafts 203 are disposed on both sides of the electric motor 202 to support the silicone belt 204.

The silicone belt 204 is rotated by the electric motor 202, and discharges the paper bag of medication that is brought into contact with the silicone belt 204 when it is rotating.

The first sensor 205 is a touch sensor determining whether or not a paper bag of medication is present in a corresponding container. The second sensor 206 is a touch sensor disposed in the region of the discharge port 134 to detect the discharge of a paper bag of medication.

Below, a detailed description will be given of a method for assisting medication in the system for assisting medication 100 with reference to the accompanying drawings.

Firstly, a process of discharging a paper bag of medication from the container 131 of the medication box 130 will be described.

Figure 6:
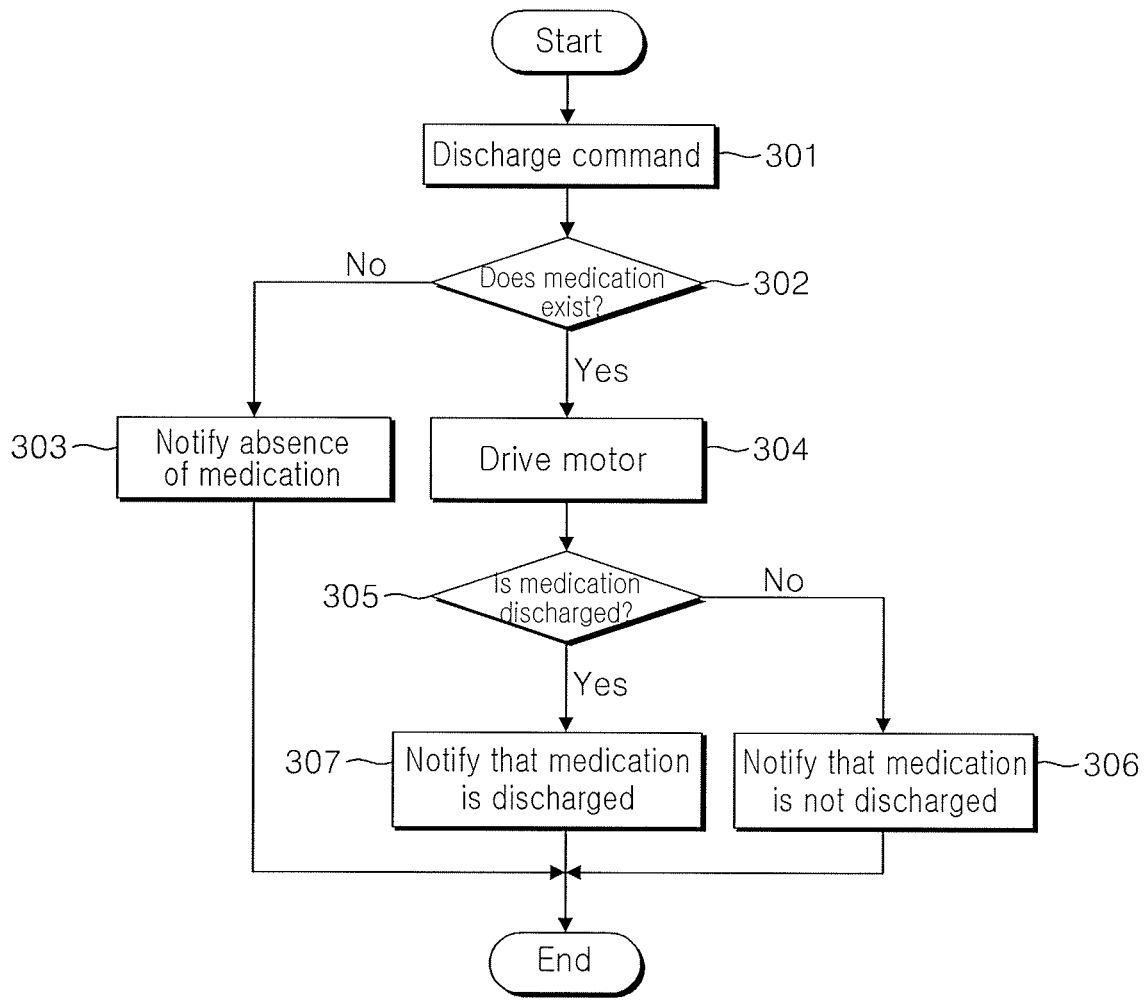
FIG. 6 is a flowchart illustrating a process of discharging a medication from the medication box in accordance with an exemplary embodiment of the invention.

FIG. 6 is a flowchart illustrating a process of discharging a medication from the medication box in accordance with an exemplary embodiment of the invention.

Referring to FIG. 6, the medication box 130 receives a discharge command from the medication service device 110 to discharge a paper bag of medication out of a specific container in step 301, and determines whether or not a dose of medication is present in the specific container in step 302. If a dose of medication is not present in the specific container as a result of the determination in step 302, the medication box 130 notifies the medication service device 110 of the absence of a dose of medication, displays the absence of medication on the display part 132, and ends the operation.

If a dose of medication is present in the specific container as a result of the determination in step 302, the medication box 130 drives the electric motor 202 to rotate the silicone belt 204 to discharge a paper bag of medication from the specific container.

In step 305, the medication box 130 determines whether or not the paper bag of medication including a dose of medication to take is discharged from the specific container. If the paper bag of medication is not discharged as a result of the determination in step 305, the medication box 130 displays, on the display part 132, the fact that the paper bag of medication has not been discharged, notifies the medication service device 110 that the paper bag of medication has not been discharged, and ends the operation. The medication box 130 can make a final determination on whether or not the paper bag of medication is discharged by repeating the foregoing steps 304 through 306 several times. The medication box 130 may facilitate medication discharge by controlling the electric motor 202 to drive the silicone belt 204 backward to a predetermined distance and then forward.

On the other hand, if the paper bag of medication is discharged as a result of the determination in step 305, the medication box 130 displays, on the display part 132, the fact that the paper bag of medication has been discharged, notifies the medication service device 110 that the paper bag of medication has been discharged, and ends the operation.

Next, a process of assisting medication in the medication service device will be described.

Figure 7:
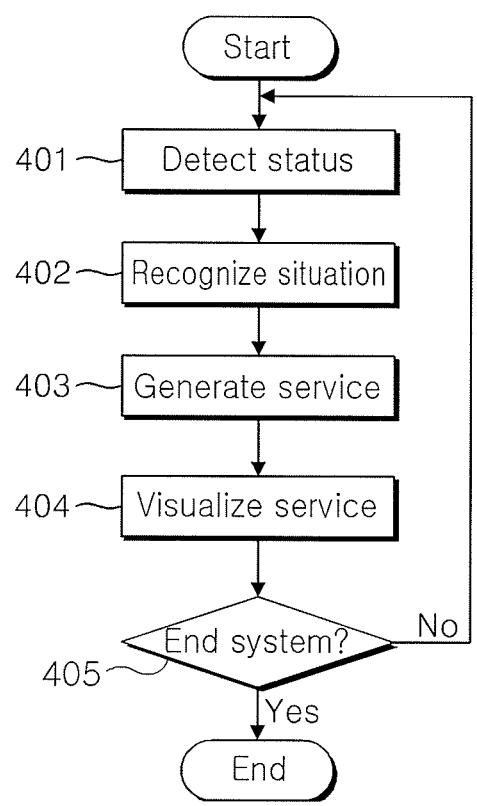
FIG. 7 is a flowchart illustrating a process of assisting medication by the medication service device in accordance with an exemplary embodiment of the invention.

FIG. 7 is a flowchart illustrating a process of assisting medication by the medication service device in accordance with an exemplary embodiment of the invention.

Referring to FIG. 7, in step 401, the medication service device 110 detects the status of a respective individual and a corresponding medication box 130 and transfers detected status data to the situation recognizer 113. Specifically, in order to detect the status of the user, the medication service device 110 checks an ID of a user and a distance from the user by analyzing an RF signal received from the user recognition device 120, and checks a medication schedule of the checked user. In addition, in order to detect the status of a medication box corresponding to the identified individual, the medication service device 110 checks an ID of the medication box and detects a container status (i.e., whether or not a dose of medication is present), a button (i.e., whether or not the button is pushed), a motor (i.e., whether or not the motor is rotating), an LCD and so on.

In step 402, the medication service device 110 recognizes a medication situation based on status data transferred from the situation sensor 111.

Figure 8:
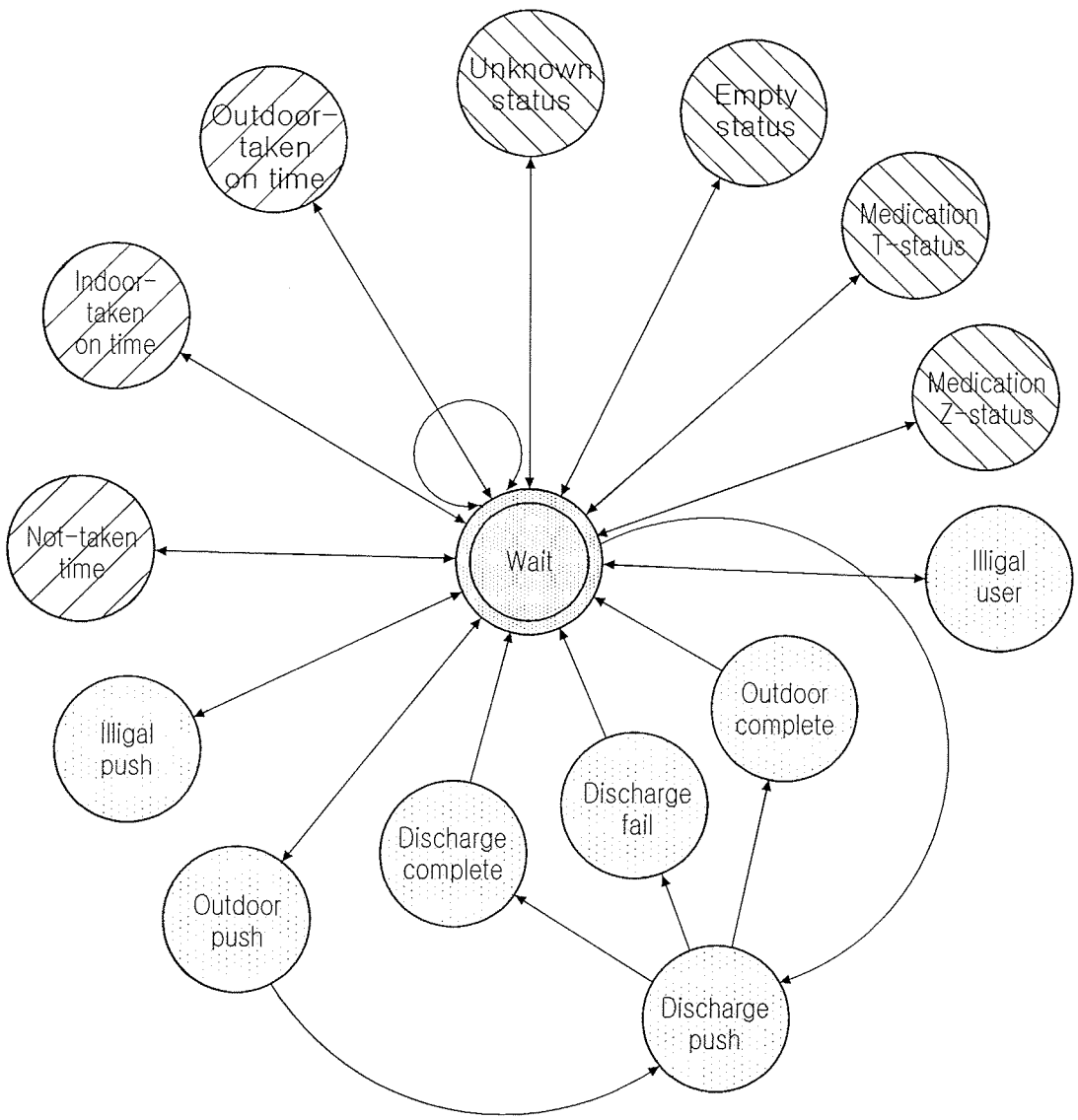
FIG. 8 is a transfer diagram illustrating a medication situation in accordance with an exemplary embodiment of the invention.

In step 403, the medication service device 110 determines a next status according to currently-detected status data and a previous medication situation using a transfer diagram relating to a medication situation as shown in FIG. 8.

The medication service device 110 generates a service capable of assisting medication in the individual utilizing the service according to the above determined status in step 403, and visualizes the generated service using a voice, an image, a short message, an LED, medication discharge, etc. in step 404.

In step 405, the medication service device 110 checks whether or not the system has stopped, and if the system has not stopped, returns to step 401 and repeats the proceeding steps. On the other hand, if the system has stopped, the operation of the medication service device 110 for assisting medication ends the operation.

In this method for assisting medication, respective steps will be described in detail as follows. Firstly, a description will be given of a detailed process of the situation sensor 111 of the medication service device 110 detecting the status of a respective user and a corresponding medication box.

Figure 9:
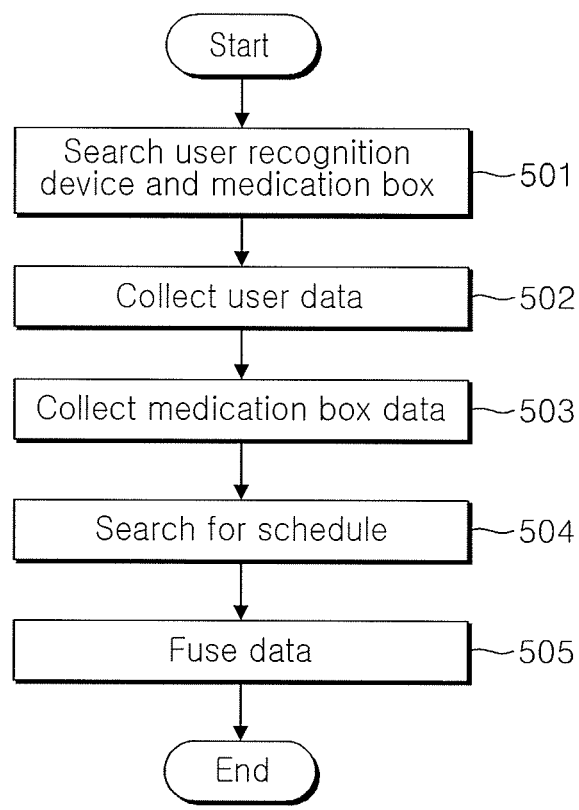
FIG. 9 is a flowchart illustrating a process of detecting the status of a user and a corresponding medication box in accordance with an exemplary embodiment of the invention.

FIG. 9 is a flowchart illustrating a process of detecting the status of a user and a corresponding medication box in accordance with an exemplary embodiment of the invention.

Referring to FIG. 9, the situation sensor 111 searches for the user recognition device 120 and the medication box 130 in step 501.

Then, in step 502, the situation sensor 111 collects user status data, such as a user ID and a distance from a user, from the searched user recognition device 120. In step 503, the situation sensor 111 collects medication box status data from the searched medication box 130. The medication box status data may include an LCD message, a container status indicating whether or not a dose of medication is present in a respective container, a motor status (i.e., whether or not the motor is rotating), a button status (i.e., whether or not the button is pushed), a medication discharge status and so on.

Afterwards, the situation sensor 111 searches for a medication schedule of the corresponding individual in step 504, and fuses the data in step 505. Specifically, the situation sensor 111 collects only necessary status data for the individual and sends the collected data to the situation recognizer 113.

Next, a description will be given of a detailed process of recognizing a medication situation using status data detected by the situation recognizer 113 of the medication service device 110.

Figure 10:
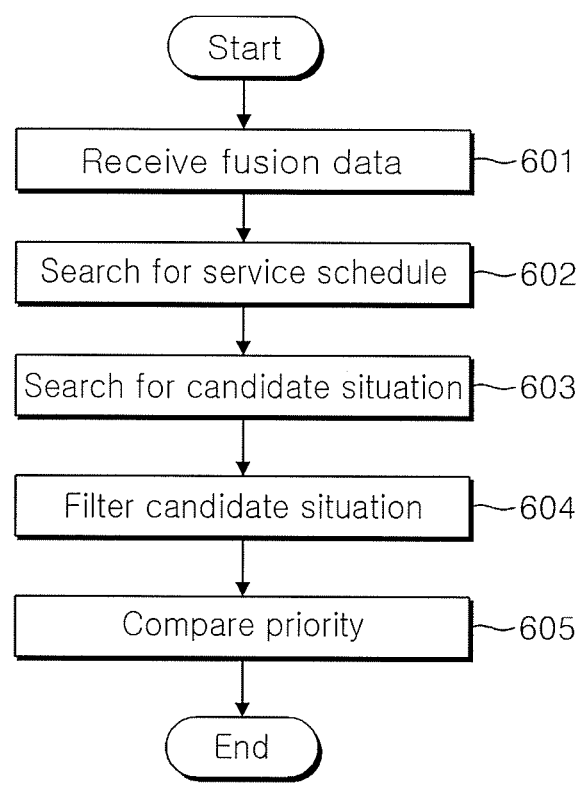
FIG. 10 is a flowchart illustrating a process of recognizing a medication situation in accordance with an exemplary embodiment of the invention.

FIG. 10 is a flowchart illustrating a process of recognizing a medication situation in accordance with an exemplary embodiment of the invention.

Referring to FIG. 10, the situation recognizer 113 receives necessary status data (hereinafter, referred to as fusion data) from the situation sensor 111 in step 601, and searches for a medication schedule to be serviced at present using the received status data in step 602. The schedule-searching step is carried out to preferentially select the oldest medication schedule of a group of schedule data, which has not been serviced until now, or a medication schedule for a specific container, the button of which is currently pushed (i.e., to which a discharge command has been given). For this, one embodiment of the invention uses search indices for schedules.

In step 603, the situation recognizer 113 searches for candidate medication situations, which can arrive at this situation, from the transfer diagram for a medication situation shown in FIG. 8.

Then, the situation recognizer 113 filters only the candidate situations satisfying conditions of the fusion data in step 604, compares the priority of the filtered situations in step 605, and ends the operation. Specifically, the situation recognizer 113 determines a situation with the highest priority of the filtered situations as a final medication situation.

Finally, a detailed process of generating and visualizing a service in the service executor 114 of the medication service device 110 will be described as follows.

Figure 11:
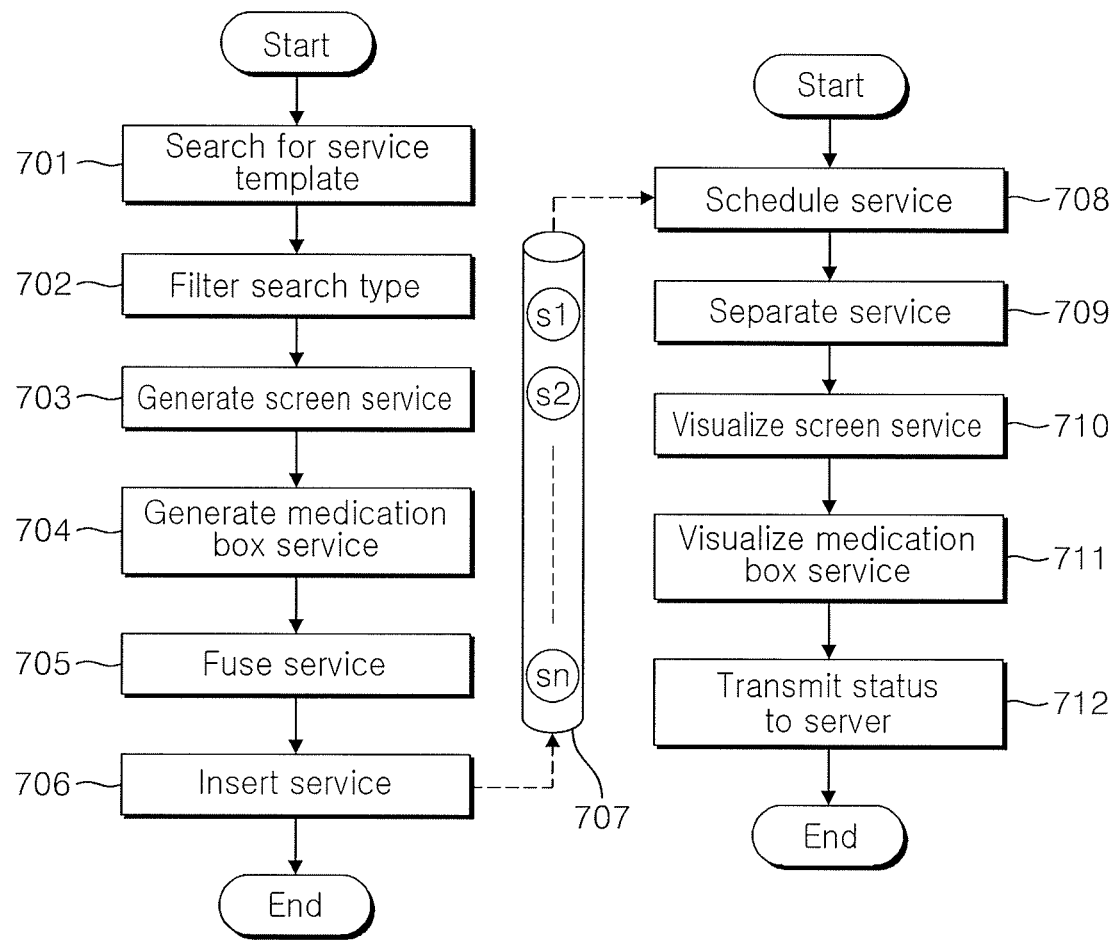
FIG. 11 is a flowchart illustrating a process of generating and visualizing a service in accordance with an exemplary embodiment of the invention.

FIG. 11 is a flowchart illustrating a process of generating and visualizing a service in accordance with an exemplary embodiment of the invention.

Describing the generation of a service with reference to FIG. 11, the service executor 114 searches for a template matching the present situation from a group of templates constructed by Extensible Markup Language (XML) in step 701.

In step 702, the service executor 114 filters only a service item that is currently set in the system for assisting medication.

In step 703, the service executor 114 generates a screen service by forming contents of items to be displayed on a screen using filtered service items. Specifically, the service executor 114 generates the screen service by combining the contents, such as a user name, a medication time and method and medication position, with an image, message and voice service template. Then, in step 704, the service executor 114 generates a medication box service by forming service contents to be displayed on the medication box using the filtered service items, the service contents including an LED corresponding to a button, an LCD message and an indication of the discharge status of a dose of medication.

Subsequently, the service executor 114 fuses the generated screen service and medication box service into one service unit in step 705, inserts the fused services into a service queue 707 in step 706, and ends the operation.

Describing service visualization with reference to FIG. 11, the service executor 114 makes up schedules for services read from the service queue 707 in step 708. Specifically, the service executor 114 extracts specific services by omitting overlapping services from the read services and scheduling the remaining services according to priorities and service times.

In step 709, the service executor 114 divides the screen service and the medication box service in the extracted services. In step 710, the service executor 114 visualizes the screen service including service items to be displayed on the screen and visualizes the medication box service on the medication box LED, LCD and motor.

Afterwards, the service executor 114 transmits the serviced medication situation of the individual to the server 140 in step 712, and ends the operation.

In the meantime, the medication service device 110 of the system for assisting medication 100 in accordance with an exemplary embodiment of the invention can automatically generate medication schedules. Below, a description will be given of a process of generating the medication schedules.

Firstly, the medication service device 110 prescribes a time for each container 131 of the medication box 130, and prescribes a number of doses and a period of doses. Then, necessary information such as precautions and a medication-taking method is inputted from a person concerned such as a doctor, a pharmacist, a nurse or a family member to the medication service device 110, and the date and time to start a medication service are inputted to the medication service device 110. Accordingly, the medication service device 110 automatically generates medication schedules by date on the basis of inputted data and stores the generated schedules in a memory (not shown).

While the present invention has been shown and described with reference to the certain exemplary embodiments thereof, it will be understood by those skilled in the art that various changes in form and details may be made therein without departing from the spirit and scope of the present invention as defined by the appended claims and their equivalents.

What is claimed is:

1. A medication service device comprising:
a situation detector detecting a status of a user based on user identification and signal strength included in a radio frequency signal, received from a user recognition device carried by the user, and a status of a medication box storing a paper bag of medication;
a situation recognizer recognizing a medication situation based on status data detected by the situation detector; and
a service executor generating a service for medication based on the recognized medication situation and affording the generated service.

2. The medication service device of claim 1, further comprising a schedule generator automatically generating a medication schedule using prescription data of a medication to be taken by the user.

3. The medication service device of claim 1, wherein the situation detector recognizes a user matching the user identification using a predetermined user table in order to detect the status of the user, recognizes a distance from and a situation in relation with the user based on the signal strength using a predetermined signal strength table, and searches for a medication schedule for the recognized user.

4. The medication service device of claim 1 wherein the status is one of adjacent indicating that the user is adjacent the medication box, confirmed indicating that the user can recognize a medication service, and not confirmed indicating that the user cannot be provided with a medication service.

5. A method for assisting medication by a medication box in a system for assisting medication, which includes the medication box storing paper bags of medication and a medication service device, the method comprising:
when a discharge command is received according to a medication schedule generated by the medication service device, detecting whether or not a paper bag of medication exists in a corresponding container using a sensor disposed in the container;
if a paper bag of medication is detected in the container, driving an electric motor disposed inside the container and discharging the paper bag of medication using a rotational force of the electric motor; and
detecting whether or not the paper bag has been discharged and providing a notification service according to a result of detection.

6. A medication box comprising:
a plurality of containers each having a cover and an input port formed in the cover, through which a paper bag of medication is inputted, wherein each of the containers stores the paper bag of medication, detects a presence of the stored paper bag of medication, and if the stored paper bag of medication is present, discharges the stored paper bag of medication according to a medication schedule;
a discharge port discharging the paper bag of medication from the container;
a button discharging the paper bag of medication stored in the container; and
a display notifying the discharge of the paper bag of medication,
wherein the containers comprise:
a silicone belt rotating and discharging the stored paper bag of medication by friction;
an electric motor rotating the silicone belt;
a first sensor detecting the existence of the stored paper bag of medication;
a second sensor disposed on a portion connected to the discharge portion, for detecting the paper bag of medication; and
a container controller controlling the discharge of the paper bag of medication according to the medication schedule, and transmitting a present status of the medication box to a medication service device.

7. An apparatus for assisting medication comprising:
a medication box comprising a plurality of containers each storing a paper bag of medication, wherein the medication box discharges a paper bag of medication from a corresponding one of the containers using a rotational force of an electric motor, and detects whether or not the stored paper bag of medication is present and whether or not the stored paper bag of medication is discharged; and
a medication service device, wherein the medication service device comprises:
a situation detector detecting a status of a user based on user identification and signal strength included in a radio frequency signal, received from a user recognition device carried by the user, and a status of the medication box;
a situation recognizer recognizing a medication situation based on status data detected by the situation detector; and
a service executor generating a service for medication based on the recognized medication situation and affording the generated service.

8. The apparatus of claim 7, wherein the medication service device provides a service for medication via a portable device when the user is out.

9. The apparatus of claim 7, wherein the medication service device further comprises a schedule generator automatically generating a medication schedule using prescription data of a medication to be taken by the user.

10. A method for assisting medication by a medication service device in a system for assisting medication, which includes the medication service device and a medication box storing paper bags of medication, the method comprising:
detecting a status of a user and a status of the medication box;
recognizing a medication situation based on detected status data, wherein the medication situation is one of adjacent indicating that the user is adjacent the medication box, confirmed indicating that the user can recognize a medication service, and not confirmed indicating that the user cannot be provided with a medication service;

generating a service according to the recognized medication situation; and visualizing and providing the generated service.

11. The method of claim 10, further comprising automatically generating a medication schedule for the user.

12. The method of claim 10, wherein detecting a status of a user and a status of the medication box comprises:

searching for the status of the user and the status of the medication box;

collecting the searched status data of the user via a radio frequency signal received from a user recognizer carried on the searched user;

collecting the status data of the searched medication box;

searching for a medication schedule for the searched user; and collecting and transmitting data necessary for the user to recognize the medication situation.

13. The method of claim 10, wherein detecting a status of a user and a status of the medication box comprises:

recognizing a user matching user identification included in the detected status data using a predetermined user table;

recognizing a distance from and a situation in relation to the user based on signal strength included in the detected status data using a predetermined signal strength table; and searching for a medication schedule for the recognized user.

14. The method of claim 10, wherein the status data of the searched medication box includes medication box identification, whether or not stored medication is present, whether or not a button is pushed, whether or not an electric motor is rotating and information about a display.

15. The method of claim 10, wherein recognizing a medication situation based on detected status data comprises:

searching for a medication schedule to be currently serviced using the detected status data;

searching for candidate medication situations using the detected status data;

filtering only candidate medication situations satisfying conditions of necessary data of the searched candidate medication situations; and recognizing one of the filtered candidate medication situations with highest priority as a final medication situation.

16. The method of claim 10, wherein generating a service according to the recognized medication situation comprises:

searching for templates matching the recognized medication situation from a group of medication service templates;

filtering templates for corresponding service items from the searched templates;

generating a screen service by combining contents of an item to be displayed on a screen with a corresponding one of the filtered templates;

generating a medication box service by combining the contents of the medication box with a corresponding one of the filtered templates;

fusing the generated screen service and the medication box service into one service unit; and storing the fused service into a service queue.

17. The method of claim 16, wherein visualizing and providing the generated service comprises:

extracting a service by omitting overlapping services from services outputted from the service queue and scheduling remaining services according priority and service time;

dividing the screen service and the medication box service in the extracted service;

visualizing service items of the divided screen service to be displayed on the screen; and executing contents for the divided medication box service.

18. The method of claim 5 wherein the electric motor drives a medication discharge belt backwards a predetermined distance if it is determined that the paper bag has not been discharged.

19. The method of claim 5, further comprising, if a paper bag of medication is not detected in the container, providing a service of notifying absence of medication.

* * * * *